United States Patent [19]

Palladino et al.

[11] Patent Number: 5,055,447
[45] Date of Patent: Oct. 8, 1991

[54] METHOD AND COMPOSITIONS FOR THE TREATMENT AND PREVENTION OF SEPTIC SHOCK

[75] Inventors: Michael A. Palladino, Foster City; Stephen A. Sherwin, San Francisco, both of Calif.

[73] Assignee: Genentech, Inc., South San Francisco, Calif.

[21] Appl. No.: 371,484

[22] Filed: Jun. 27, 1989

Related U.S. Application Data

[63] Continuation-in-part of Ser. No. 225,502, Jul. 28, 1988, abandoned.

[51] Int. Cl.$^5$ .............................................. A61K 37/02
[52] U.S. Cl. ...................................... 514/12; 530/397; 530/399
[58] Field of Search ................. 530/397, 399; 514/12, 514/8

[56] References Cited

U.S. PATENT DOCUMENTS 4,806,652  2/1989  Bentz et al. ............................... 514/2
4,886,747  12/1989  Derynck et al. ...................... 435/69.4

FOREIGN PATENT DOCUMENTS 0213776  3/1987  European Pat. Off. .
0261599  3/1988  European Pat. Off. .
0269408  6/1988  European Pat. Off. .

OTHER PUBLICATIONS

Sharples et al., DNA 6(3) pp. 239-244 (1987).
Madisen DNA 7(1) pp. 1-8 (1988).
Ranges et al., J. Exp. Med., 166: 991-998 (1987).
Roberts and Sporn, "The Transforming Growth Factor-Betas", in Peptide Growth Factors and Their Receptors, ed. M. Sporn and A. Roberts, Handbook of Experimental Pharmacology, Springer-Verlag, Heidelberg, 1989.
Chua et al., J. Biol. Chem., 260:5213-5216 (1983).
Tashjian et al., Proc. Natl. Acad. Sci. U.S.A., 82:4535-4538 (1985).
Brinkerhoff et al., Arthritis and Rheumatism, 26:1370-1379 (1983).
Beutler et al., Science, 232:977-980 (1986).
Espevik et al., J. Exp. Med. 166:571-576 (1987).
Beutler et al., New Eng. J. Med. 316:379ff (1987).
Kehrl et al., J. Exp. Med. 163: 1037-1050 (1986).
Ristow, Proc. Natl. Acad. Sci. U.S.A. 83:5531-5533 (1986).
Rook et al., J. Immunol. 136:3916-3920 (1986).
Sporn et al., Science 233:532-534 (1986).
Hesse et al., Surg. Gynecol. Obstet. 166: 147-153 (1988).
Michie et al., New Eng. J. Med. 318:1481-1486 (1988).
Espevik et al., J. Immunol. 140:2312—2316 (1988).
Beutler et al., Science 229:869-871 (1985).
Tracey et al., Nature 330:662-664 (1987).
Urbaschek et al., Rev. Infect. Dis. 9:S607-S615 (1987).

Primary Examiner—Margaret Moskowitz
Assistant Examiner—Shelly J. Guest
Attorney, Agent, or Firm—Janet E. Hasak

[57] ABSTRACT

Methods and compositions are provided for the treatment or prophylaxis of septic shock caused by bacteremic infection. Therapeutically and prophylactically effective doses of transforming growth factor-beta are administered to patients, either alone or in combination with another therapeutic or prophylactic agent for treating this pathologic condition. Preferably, the transforming growth factor-beta is human transforming growth factor-beta, and most preferably TGF-$\beta_1$, TGF-$\beta_2$, or TGF-$\beta_3$.

9 Claims, 15 Drawing Sheets

FIG. 1a

```
1   CCAGCAGGAC CTGTTTAGAC ACATGGAGAA GAAACCCAGA GCTTCAAGGC ACACAGTCGG CTTCTTCGTG

71  CTCAGGGTTG CCAGCGCTTC CTGGAAGTCC TGAAGCTCTC GCAGTGCAGT GAGTTCATGC ACCTTCTTGC

141 CAAGCCTCAG TCTTCGGGAT CTAGGGAGGC CGCCTGGTTT TCCTCCCCTCC TTCTGCACGT CGGCTGGGGT

MET HIS LEU
211 CTCCTCCTCA CCAGGCCTCG CAGCCCCCGG GCCTCTCTCC CCGGCTCACG CATGAAG    ATG CAC TTG 10                        20                        40
    GLN ARG ALA LEU VAL VAL LEU ALA LEU LEU LEU ASN PHE ALA THR VAL SER LEU SER MET
277 CAA AGG GCT CTG GTG GTC CTG GCC CTG CTG CTG AAC TTT GCC ACG GTC AGC CTC TCC ATG 30                                  40
    SER THR CYS THR THR LEU ASP PHE ASP HIS ILE LYS ARG LYS ARG VAL GLU ALA ILE
334 TCC ACT TGC ACC ACC TTG GAC TTC GAC CAC ATC AAG AGG AAG AGG GTG GAA GCC ATT 50                                  60
    ARG GLY GLN ILE LEU SER LYS LEU ARG LEU THR SER PRO PRO ASP PRO SER MET LEU
391 AGG GGA CAG ATC TTG AGC AAA CTC AGG CTC ACC AGT CCC GAT CCA TCG ATG TTG
```

FIG.1a(I)

```
                 ALA ASN ILE PRO THR GLN VAL LEU ASP TYR ASN SER THR ARG GLU LEU LEU GLU
448              GCC AAC ATC CCC ACC CAG GTC CTG GAC CTT AAC AGC ACC CGG GAG CTG CTG GAG
                                                    70
      GLU VAL HIS GLY GLU ARG GLY ASP ASP CYS THR GLN GLU ASN THR GLU SER GLU TYR
505   GAG GTG CAC GGG GAG AGG GGA GAC GAC TGC ACT CAG GAA AAC ACC GAG TCG GAG TAC
           80                                    90
      TYR ALA LYS GLU ILE TYR LYS PHE ASP MET ILE GLN GLY LEU GLU GLU HIS ASN ASP
562   TAT GCC AAG GAA ATC TAT AAA TTC GAC ATG ATC CAG GGG CTG GAG GAG CAC AAT GAT
                     100                                    110
      LEU ALA VAL CYS PRO LYS GLY ILE THR SER LYS ILE PHE ARG PHE ASN VAL SER SER
619   CTG GCC GTT TGC CCC AAA GGA ATC ACC TCC AAG ATT TTC CGC TTC AAC GTG TCG TCA
                            120                                    130
      VAL GLU LYS ASN GLU THR ASN LEU PHE ARG ALA GLU PHE ARG VAL LEU ARG MET PRO
676   GTG GAG AAA AAC GAA ACC AAC CTG TTC CGG GCA GAA TTC CGG GTC TTG CGG ATG CCC
                        140                                        150
```

FIG.1a(II)

```
                      160
      ASN PRO SER SER LYS ARG SER GLU GLN ARG ILE GLU LEU PHE GLN ILE LEU GLN PRO
733   AAC CCC AGC AGC AAG CGC AGC GAG CAG AGG ATT GAG CTC TTC CAG ATC CTC CAG CCC 180                                      190
      ASP GLU HIS ILE ALA LYS GLN ARG TYR ILE ASP GLY LYS ASN LEU PRO THR ARG GLY
790   GAT GAG CAC ATA GCC AAG CAG CGC TAC ATC GAC GGC AAG AAC CTG CCC ACG CGG GGT 200                                      210
      ALA ALA GLU TRP LEU SER PHE ASP VAL THR ASP THR VAL ARG GLU TRP LEU LEU ARG
847   GCC GCC GAG TGG CTG TCC TTC GAC GTC ACA GAC ACT GTG CGT GAA TGG CTG CTG AGA 220                                      230
      ARG GLU SER ASN LEU GLY LEU GLU ILE SER ILE HIS CYS PRO CYS HIS THR PHE GLN
904   AGA GAA TCC AAC TTG GGT CTG GAA ATC AGC ATT CAT TGT CCG TGT CAC ACC TTT CAG 240                                      250
      PRO ASN GLY ASP ASP ILE LEU GLU ASN ILE GLN GLU VAL MET GLU ILE LYS PHE LYS GLY
961   CCC AAC GGG GAT GAT ATC TTG GAA AAC ATT CAA GAG GTG ATG GAA ATC AAA TTC AAA GGT

260
      VAL ASP SER GLU ASP ASP PRO GLY ARG GLY ASP LEU GLY ARG LEU LYS LYS LYS LYS
1018  GTG GAC AGT GAG GAT GAT CCG GGC CGT GGA GAC CTG GGG CGA CTT AAG AAG AAG AAG
```

FIG.1a(III)

```
              270                       280
     GLU HIS SER PRO HIS LEU ILE LEU MET MET ILE PRO PRO ASP ARG LEU ASP ASN PRO
1075 GAA CAC AGC CCT CAT CTA ATC CTC ATG ATG ATT CCT CCA GAC CGG CTA GAC AAC CCA
                                     +           +           +
                                                300
     GLY LEU GLY ALA GLN ARG LYS LYS ARG ALA LEU ASP THR ASN TYR CYS PHE ARG ASN
1132 GGC CTG GGG GCT CAG AGG AAG AAG CGG GCC CTG GAC ACC AAC TAC TGC TTC CGC AAT
              310                                       320
     LEU GLU GLU ASN CYS CYS VAL ARG PRO LEU TYR ILE ASP PHE ARG GLN ASP LEU GLY
1189 TTG GAG GAG AAC TGC TGT GTG CGC CCT CTC TAC ATT GAC TTC CGA CAG GAT CTG GGC
                            330                                       340
     TRP LYS TRP VAL HIS GLU PRO LYS GLY TYR TYR ALA ASN PHE CYS SER GLY PRO CYS
1246 TGG AAG TGG GTC CAT GAA CCT AAG GGC TAC TAT GCC AAC TTC TGC TCA GGC CCT TGC
                                          350                                       360
     PRO TYR LEU ARG SER ALA ASP THR THR HIS SER SER VAL LEU GLY LEU TYR ASN THR
1303 CCG TAC CTC CGC AGT GCA GAC ACA ACC CAC AGC TCG GTG CTG GGG CTG TAC AAC ACC
                      370                                       380
     LEU ASN PRO GLU ALA SER PRO CYS CYS VAL PRO GLN ASP LEU GLU PRO LEU
1360 CTG AAC CCC GAA GCC TCT CCG TGC TGC GTG CCC CAG GAC CTG GAG CCC CTG
```

FIG.1a(IV)

```
                                                390                                      400
      THR ILE LEU TYR TYR VAL GLY ARG THR ALA LYS VAL GLU GLN LEU SER ASN MET VAL
1417  ACC ATC CTG TAC TAC GTC GGG AGG ACC GCC AAG GTG GAG CAG CTC TCT AAC ATG GTG

VAL LYS SER CYS LYS CYS SER
1474  GTG AAG TCC TGC AAG TGC AGC TGA GCC CCGCCTGCCA CCCAGAGAGG GAGGAGAATT GCCACTGCCT

1541  GCCTGCCTGC TCCTCGGGAA ACACAAAAGC AACAGACCTC ACCTCGAGGC CTGGAGCCCA CAACCTTCAG

1611  CTCCACGCAA GTGGCCGAGA CGGAGGTTCC CTTTCGGAAC ATTTCTCTTT CTTGCTGGCT CTGAGAATCA

1681  CTGTAGTAAA GAAAGTGTGG GTTTGATTAG GGGAAGGTTG AACTCTTCAG AACACACGGA TTTTCTGTGA

1751  CGTAGACAGA GGTGGTGGGG ACAGAGGAAG AGGGATGGCA AGCGGATGCC GCGTGGGGCC ATGGGATTTG

1821  GGATACCCAA GGGAGGAGGA AGGGCAGAGA ATGGCCAGGA CAGGGCCAGA CTGGAAGATG CTTGGAGCTG

1891  AGGTCAGATG GCTCATCGCC GCCCCAAGTC TGCTCTAGGG AATCTGGATT AGTCATATACA AGGCAAGTGT

1961  TTTTCTTCAG ACAGGTTCCC AAGACAAAGT CCCAGAACTG TACCTTATAC TTACCTGGGG TTAAGGACAA

2031  ATCTGTTAGT TTTGCAAATT GTCCCATGGA CATCAGTCAG CATCAAGGGT CACTACAGGG AGAAAATCCA
```

```
TCCCGGGCC GTCCACTATA TTGGGCCCTA TGGATATGCT GAACTCAGAA GCAGAGGGTG GTG

CTCTCTGTT CTGCCCCCTG GGTTCCTCCT CTCGCCCTTCT TCCTCGATTG TATTTCTCCT CCT

CTAGACACC TTCCAGGTCA GGGGCACAT TTCTGGAGTG TGGGTCTGTG CAGCCCTGGG GGG

TCCTCTCC TGACCCCTCT AAGACCTTGT GCTCATCTGG TGTTCCTGGA AGCAGGTGCT CCT

GGCGTGCGG GGAAATTGCA CACGTGCCAC ACAATGACTT GGCCCCAGAT GCATAGACTG CTG

CAAATACAA ATATTACTCT CAAAAATCTT TGTATAAATA AATATTTTTT GGGGAATCTT TTT

TCTTCTGGA AGATTGTTTC TAAACAATAA AGGCCCTTATT CTAAGGTGTA AAAAA
```

FIG.1b

```
  1 CCTGTTTAGA CACATGGACA ACAATCCCAG CGCTACAAGG CACACAGTCC GCTTCTTCGT CCTCAGGGTT

71 GCCAGCGCTT CCTGGAAGTC CTGAAGCTCT CGCAGTGCAG TGAGTTCATG CACCTTCTTG CCAAGCCTCA

141 GTCTTTGGGA TCTGGGGAGG CCGCCTGGTT TCCCTCCCTC CTTCTGCACG TCTGCTGGGG TCTCTTCCTC

MET HIS LEU GLN ARG
211 TCCAGGCCTT GCCGTCCCCC TGGCCTCTCT TCCCAGCTCA CACATGAAG  ATG CAC TTG CAA AGG
                                                                                        20
    ALA LEU VAL VAL LEU ALA LEU LEU ASN PHE ALA THR VAL SER LEU SER THR
276 GCT CTG GTG GTC CTG GCC CTG CTG AAC TTT GCC ACG GTC AGC CTC TCT CTG TCC ACT
                    30                                      40
    CYS THR THR LEU ASP PHE GLY HIS ILE LYS LYS ARG VAL GLU ALA ILE ARG GLY
333 TGC ACC ACC TTG GAC TTC GGC CAC ATC AAG AAG AGG GTG GAA GCC ATT AGG GGA
                                            50                                  60
    GLN ILE LEU SER LYS LEU ARG LEU THR SER PRO PRO THR VAL MET THR HIS
390 CAG ATC TTG AGC AAG CTC AGG CTC ACC AGC CCC CCT GAG CCA ACG GTG ATG ACC CAC
                                70                                                  80
    VAL PRO TYR GLN VAL LEU ALA LEU TYR ASN SER THR ARG GLU LEU LEU GLU MET
447 GTC CCC TAT CAG GTC CTG GCC CTT TAC AAC AGC ACC CGG GAG CTG CTG GAG GAG ATG
```

FIG.1b(I)

```
                                                              90                      100
      HIS GLY ARG GLU GLU GLY CYS THR GLN GLU ASN THR GLU SER GLU TYR TYR ALA
504   CAT GGG AGG GAG GAA GGC TGC ACC CAG GAA AAC ACC GAG TCG GAA TAC TAT GCC

110
      LYS GLU ILE HIS LYS PHE ASP MET ILE GLN ILE GLY LEU ALA GLU HIS ASN GLU LEU ALA
561   AAA GAA ATC CAT AAA TTC GAC ATG ATC CAG ATC GGG CTG GCG GAG CAC AAC GAA CTG GCT 120                              130
      VAL CYS PRO LYS GLY ILE THR SER LYS VAL PHE ARG PHE ASN VAL SER SER VAL GLU
618   GTC TGC CCT AAA GGA ATT ACC TCC AAG GTT TTC CGC TTC AAT GTG TCC TCA GTG GAG 140                                      150
      LYS ASN ARG THR ASN LEU PHE ARG ALA GLU PHE ARG VAL LEU ARG VAL PRO ASN PRO
675   AAA AAT AGA ACC AAC CTA TTC CGA GCA GAA TTC CGG GTC TTG CGG GTG CCC AAC CCC 160                              170
      SER SER LYS ARG ASN GLU GLN ARG ILE GLU GLN LEU PHE GLN ILE LEU ARG PRO ASP GLU
732   AGC TCT AAG CGG AAT GAG CAG AGG ATC GAG CTC TTC CAG ATC CTT CGG CCA GAT GAG 180                              190
      HIS ILE ALA LYS GLN ARG TYR ILE GLY LYS ASN LEU PRO THR ARG GLY THR ALA
789   CAC ATT GCC AAA CAG CGC TAT ATC GGT GGC AAG AAT CTG CCC ACA CGG GGC ACT GCC 200                                      210
      GLU TRP LEU SER PHE ASP VAL THR ASP THR VAL ARG GLU TRP LEU ARG ARG GLU
846   GAG TGG CTG TCC TTT GAT GTC ACT GAC ACT GTG CGT GAG TGG CTG AGA AGA GAG
```

FIG.1b(II)

```
                              220                        230
     SER ASN LEU GLY LEU GLU ILE SER ILE HIS CYS PRO HIS THR PHE GLN PRO ASN
 903 TCC AAC TTA GGT CTA GAA ATC AGC ATT CAC TGT CCA CAC ACC TTT CAG CCC AAT 240                        250
     GLY ASP ILE LEU GLU ASN ILE HIS GLU VAL MET GLU ILE LYS PHE LYS GLY VAL ASP
 960 GGA GAT ATC CTG GAA AAC ATT CAC GAG GTG ATG GAA ATC AAA TTC AAA GGC GTG GAC 260                        270
     ASN GLU ASP ASP HIS GLY ARG ASP LEU GLY ARG LEU LYS LYS GLN LYS ASP HIS
1017 AAT GAG GAT GAC CAT GGC CGT GGA GAT CTG GGG CGC AAG AAG CAG AAG GAT CAC 280                        290
     HIS ASN PRO HIS LEU ILE LEU MET MET ILE PRO PRO HIS ARG LEU ASP ASN PRO GLY
1074 CAC AAC CCT CAT CTA ATC CTC ATG ATG ATT CCC CCA CAC CGG CTC GAC AAC CCG GGC

300
     GLN GLY GLY GLN ARG LYS LYS ARG ALA LEU ASP THR ASN TYR CYS PHE ARG ASN LEU
1131 CAG GGG GGT CAG AGG AAG AAG CGG GCT TTG GAC ACC AAT TAC TGC TTC CGC AAC TTG

320
     GLU GLU ASN CYS CYS VAL ARG PRO LEU TYR ILE ASP PHE ARG GLN ASP LEU GLY TRP
1188 GAG GAG AAC TGC TGT GTG CGC CCC CTC TAC ATT GAC TTC CGA CAG GAT CTG GGC TGG 330                                 340
     LYS TRP VAL HIS GLU PRO LYS GLY TYR TYR ALA ASN PHE CYS SER GLY PRO CYS PRO
1245 AAG TGG GTC CAT GAA CCT AAG GGC TAC TAT GCC AAC TTC TGC TCA GGC CCT TGC CCA
```

FIG.1b(III)

```
         350
     TYR LEU ARG SER ALA ASP THR THR HIS SER THR VAL LEU GLY LEU TYR ASN THR LEU
1302 TAC CTC CGC AGT GCA GAC ACA ACC CAC AGC ACG GTG CTG GGA CTG TAC AAC ACT CTG

360
     ASN PRO GLU ALA SER ALA SER PRO CYS CYS VAL PRO GLN ASP LEU GLU PRO LEU THR
1359 AAC CCT GAA GCA TCT GCC TCG CCT TGC TGC GTG CCC CAG GAC CTG GAG CCC CTG ACC
                                 380

400
     ILE LEU TYR TYR VAL GLY ARG THR PRO LYS VAL GLU GLN LEU SER ASN MET VAL VAL
1416 ATC CTG TAC TAT GTT GGG AGG ACC CCC AAA GTG GAG CAG CTC TCC AAC ATG GTG GTG
                     390

410
     LYS SER CYS LYS CYS SER
1473 AAG TCT TGT AAA TGT AGC TGA  GACCCCAC GTGCCGACAGA GAGAGGGGAG AGAGAACCAC CACTGCCTGA

1544 CTGCCCCGCTC CTCGGGAAAC ACACAAGCAA CAAACCTCAC TGAGAGGCCT GGAGCCCACA ACCTTCGGCT

1614 CCGGGCAAAT GGCTGAGATG GAGGTTTCCT TTTGGAACAT TTCTTTCTTG CTGGCTCTGA GAATCACGGT

1684 GGTAAAGAAA GTGTGGGTTT GGTTAGAGGA AGGCTGAACT CTTCAGAACA CACAGACTTT CTGTGACGCA

1754 GACAGAGGGG ATGGGGATAG AGGAAAAGGGA TGGTAAGTTG AGATGTTGTG TGGCAATGGG ATTTGGGCTA

1824 CCCTAAAGGG AGAAGGAAGG GCAGAGAATG GCTGGGTCAG GGCCAGACTG GAAGACACTT CAGATCTGAG
```

FIG.1b(IV)

```
1894  GTTGGATTTG CTCATTGCTG TACCACATCT GCTCTAGGGA ATCTGGATTA TGTTATACAA GGCAAGCATT

1964  TTTTTTTTTA AAGACAGGTT ACGAAGACAA AGTCCCAGAA TTGTATCTCA TACTGTCTGG GATTAAGGGC

2034  AAATCTATTA CTTTTGCAAA CTGTCCTCTA CATCAATTAA CATCGTGGGT CACTACAGGG AGAAAATCCA

2104  GGTCATGCAG TTCCTGGCCC ATCAACTGTA TTGGGCCTTT TGGATATGCT GAACGCAGAA GAAAGGGTGG

2174  AAATCAACCC TCTCCTGTCT GCCCTCTGGG TCCCTCCTCT CACCTCTCCC TCGATCATAT TTCCCCTTGG

2244  ACACTTGGTT AGACGCCTTC CAGGTCAGGA TGCACATTTC TGGATTGTGG TTCCATGCAG CCTTGGGGCA

2314  TTATGGGTCT TCCCCCACTT CCCCTCCAAG ACCCTGTGTT CATTTGGTGT TCCTGGAAGC AGGTGCTACA

2384  ACATGTGAGG CATTCGGGGA AGCTGCACAT GTGCCACACA GTGACTTGGC CCCAGACGCA TAGACTGAGG

2454  TATAAAGACA AGTATGAATA TTACTCTCAA AATCTTTGTA TAAATAAATA TTTTTGGGGC ATCCTGATG

2524  ATTTCATCTT CTGGAATATT GTTTCTAGAA CAGTAAAAGC CTTATTCTAA GGTG
```

FIG.1C

```
                       20                          40
hTGF.β3    MHLQRALVVLALLNFATVSLSLSTCTTLDFGHIKKKRVEAIRGQILSKLR
           ******************** .******* *** .**************
pTGF.β3    MHLQRALVVLALLNFATVSLSMSTCTTLDFDHIKRKRVEAIRGQILSKLR 60             80                    100
hTGF.β3    LTSPPEPTVMTHVPYQVLALYNSTRELLEEMHGEREEGCTQENTESEYYA
           *****.......* *** **************.****..***********
pTGF.β3    LTSPPDPSMLANIPTQVLDLYNSTRELLEEVHGERGDDCTQENTESEYYA 120                 140
hTGF.β3    KEIHKFDMIQGLAEHNELAVCPKGITSKVFRFNVSSVEKNRTNLFRAEFR
           *** ******** ***.************.************ ********
pTGF.β3    KEIYKFDMIQGLEEHNDLAVCPKGITSKIFRFNVSSVEKNETNLFRAEFR

160        .        180                 200
hTGF.β3    VLRVPNPSSKRNEQRIELFQILRPDEHIAKQRYIGGKNLPTRGTAEWLSF
           *** .********.***********.************.*******.******
pTGF.β3    VLRMPNPSSKRSEQRIELFQILQPDEHIAKQRYIDGKNLPTRGAAEWLSF 220                240
hTGF.β3    DVTDTVREWLLRRESNLGLEISIHCPCHTFQPNGDILENIHEVMEIKFKG
           ****************************************.*********
pTGF.β3    DVTDTVREWLLRRESNLGLEISIHCPCHTFQPNGDILENIQEVMEIKFKG 260                  280                300
hTGF.β3    VDNEDDHGRGDLGRLKKQKDHHNPHLILMMIPPHRLDNPGQGGQRKKR̲A̲L̲
           **.***.**********.*. *.***********.****** *.*****̲*̲*̲
pTGF.β3    VDSEDDPGRGDLGRLKKKKE-HSPHLILMMIPPDRLDNPGLGAQRKKR̲A̲L̲

320                  340
hTGF.β3    ┌──────────────────────────────────────────────────┐
           │DTNYCFRNLEENCCVRPLYIDFRQDLGWKWVHEPKGYYANFCSGPCPYLR│
           │**************************************************│
pTGF.β3    │DTNYCFRNLEENCCVRPLYIDFRQDLGWKWVHEPKGYYANFCSGPCPYLR│
           └──────────────────────────────────────────────────┘

360                  380                400
hTGF.β3    ┌──────────────────────────────────────────────────┐
           │SADTTHSTVLGLYNTLNPEASASPCCVPQDLEPLTILYYVGRTPKVEQLS│
           │******.*******************************.******│
pTGF.β3    │SADTTHSSVLGLYNTLNPEASASPCCVPQDLEPLTILYYVGRTAKVEQLS│
           └──────────────────────────────────────────────────┘ hTGF.β3    ┌─────────┐
           │NMVVKSCKCS│
           │**********│
pTGF.β3    │NMVVKSCKCS│
           └─────────┘
```

FIG.2

| | |
|---|---|
| h.β-TGF₁: | ALDTNYCFSSTEKNCCVRQLYIDFRKDLGWK-WIHEPKGY |
| h.β-TGF₃: | ALDTNYCFRNLEENCCVRPLYIDFRQDLGWK-WVHEPKGY |
| p.β-TGF₃: | ALDTNYCFRNLEENCCVRPLYIDFRQDLGWK-WVHEPKGY |
| b.β-TGF₂: | ALDAAYCFRRVQDNCCLRPLYIDFKRDLGW---------- |
| | 1　　　　　10　　　　　20　　　　　30 |

| | |
|---|---|
| h.β-TGF₁: | HANFCLGPCPYIWSLDT----QYSKVLAL-YNQ--HNPGA |
| h.β-TGF₃: | YANFCSGPCPYLRSADT----THSTVLGL-YNT--LNPEA |
| p.β-TGF₃: | YANFCSGPCPYLRSADT----THSSVLGL-YNT--LNPEA |
| b.β-TGF₂: | |
| | 40　　　　　50　　　　　60　　　　　70 |

| | |
|---|---|
| h.β-TGF₁: | SAAPCCVPQALEPLPIVYYV-GRKPKVEQLSNMIVRSCKCS |
| h.β-TGF₃: | SASPCCMPQDLEPLTILYYV-GRTPKVEQLSNMVVKSCKCS |
| p.β-TGF₃: | SASPCCVPQDLEPLTILYYV-GRTAKVEQLSNMVVKSCKCS |
| b.β-TGF₂: | |
| | 80　　　　　90　　　　　100　　　　110 |

METHOD AND COMPOSITIONS FOR THE TREATMENT AND PREVENTION OF SEPTIC SHOCK

This application is a continuation-in-part application of U.S. application Ser. No. 225,502, filed July 28, 1988, now abandoned.

BACKGROUND OF THE INVENTION

This invention relates to the treatment of patients suffering from or at risk of septic shock caused by bacteremic infections. More particularly, this invention relates to the prophylaxis of incipient septic shock and to the amelioration of the symptoms characteristic of acute septic shock.

Septic shock is a widespread and hazardous syndrome that frequently accompanies severe Gram-negative and, to a lesser degree, Gram-positive bacteremia. According to recent studies, in a hypothetical group of 100 patients who are bacteremic with Gram-negative organisms, the incidence of metabolic complications and shock is about 25%, while about 10% of patients with Gram-positive bacteremia (especially from *S. aureus* infections) develop shock.

The presence of bacteremic shock dramatically increases morbidity and mortality. In cases in which the inciting infection is localized, shock is associated with a 50% mortality. Frank shock accompanying systemic bacteremia is characterized by greater than 70% mortality. In addition, recovery from the effects of shock and bacteremia typically requires long-term intensive care at great expense.

Gram-negative rods such as Enterobacteriaceae and Pseudomonadeaceae are normal habitants of the digestive tract that invade the bloodstream of patients who receive immunosuppressive therapy or suffer from serious underlying trauma or disease, such as severe thermal burns or other serious injuries, cystic fibrosis, renal insufficiency, malignant neoplastic diseases, major surgical procedures, or organ transplantations.

The classic septic shock syndrome results primarily from the sequence of events triggered by bacteremia during which cell wall bacterial substances (endotoxin in Gram-negative organisms and the peptidoglycan/teichoic acid complex in Gram-positive organisms) activate the complement, coagulation, kinin and ACTH-/endorphin systems. This activation results in a series of metabolic events that ultimately progress to a state of shock.

Incipient septic shock is characterized by the following: Body temperature extremes (fever >40.6° C. or hypothermia), altered mental status, orthostatic blood pressure decrease (>30 mm Hg), decreasing urine output, unexplained edema usually associated with a falling serum albumin concentration, tachypnea with hypoxemia, and/or the development of a metabolic acidosis, elevated serum lactate, leukopenia (predominantly neutropenia), and thrombocytopenia with or without petechial skin rash.

Septic shock related to bacteremic infections advances in two hemodynamic stages. First, patients demonstrate symptoms characteristic of vasomotor effect following ACTH/endorphin release, kallikrein-kinin system activation, and histamine release induced by bacterial cell wall components or toxins. As these symptoms develop, complement-mediated leukoagglutination and capillary damage (primary due to the intracapillary adherence and aggregation of activated polymorphonuclear leukocytes) cause a severe capillary leak syndrome followed by a dramatic fall in intravascular blood volume, decline in cardiac output, and disseminated intravascular coagulation.

Obviously, early diagnosis and therapy of patients at risk from septic shock is desirable. At the present time, prophylactic measures include strict adherence to infection control measures, antibiotic and intravenous fluid therapy, immunoprophylaxis, and granulocyte transfusions.

Anti-shock therapy commonly includes volume replacement using plasma expanders such as 5% albumin, isotonic saline, or lactated Ringer's solution under continuous hemodynamic monitoring. Just enough fluid is supplied to bring the patient's pulmonary capillary wedge pressure to the high normal range. Vasoactive compounds such as dopamine dobutamine, norepinephrine, etc. are used when volume replacement is not sufficient. In addition, anti-inflammatory drugs such as methylprednisolone sodium succinate may be used in large doses (up to 30 mg/kg). Anti-prostaglandins have been proposed for the suppression of inflammatory damage caused by the activated peripheral polymorphonuclear leukocytes.

Finally, mortality from bacteremic infections has been reduced by using substances such as mafenide acetate or silver salts that inhibit bacterial colonization of the burn wound surface and by using potent antimicrobial agents, sympathomimetic amines, corticosteroids, anti-coagulants, granulocyte transfusion, and diuretics for treating bacteremia as primary or adjunct therapy.

Such measures, however, have only proved partially successful in controlling the morbidity and mortality associated with endotoxin or septic shock. Antibiotic therapy may possibly exacerbate incipient toxic shock by inducing the release of bacteria cell wall material and toxins. Vasopressors do not ameliorate capillary damage, anti-inflammatory therapies are controversial, and volume replacement is at best a stop-gap therapy resulting in edema and cardiac complications.

The transforming growth factor-$\beta$ molecules identified thus far are two-chain molecules containing two identical 112 residue polypeptide chains linked by disulfide bonds. The molecular mass of these dimers is about 25 kd. Biologically active TGF-$\beta$ has been defined as a molecule capable of inducing anchorage independent growth of target cell lines or rat fibroblasts in in vitro cell culture, when added together with EGF or TGF-$\alpha$ as a co-factor. Suitable methods are known for purifying TGF-$\beta$ from platelets or placenta, for producing it in recombinant cell culture and for determining its activity. See, for example, R. Derynck et al., *Nature*, 316:701 (1985) and U.S.S.N.s 715,142; 500,832; 500,833, all abandoned; European Pat. Pub. Nos. 200,341 published Dec. 10, 1986, published Jan. 22, 1986, 268,561 published May 25, 1988, and 267,463 published May 18, 1988; GB Pat. Appln. 2,146 335 published Apr. 17, 1985; U.S. Pat. No. 4,774,322; Seyedin et al, *J. Biol. Chem.*, 262: 1946-1949 (1987); and Cheifetz et al, *Cell* 48: 409-415 (1987), the entire contents thereof being expressly incorporated by reference.

TGF-$\beta$ has been shown to have numerous regulatory actions on a wide variety of both normal and neoplastic cells. Recent studies indicate an important role for TGF-$\beta$ in cells of the immune system (J. Kehrl et al., *J. Exp. Med.*, 163:1037 [1986]; H-J. Ristow, *Proc. Natl.*

Acad. Sci. U.S.A., 83: 5531 [1986]; and A. Rook et al., J. Immunol., 136:3916 [1986]) and connective tissue (M Sporn et al., Science, 219:1329 [1983]; R. Ignotz et al., J. Biol. Chem., 261:4337 [1986]; J. Varga et al., B.B.Res.-Comm., 138:974 [1986]; A. Roberts et al., Proc. Natl Acad. Sci. U.S.A., 78:5339 [1981]; A. Roberts et al., Fed Proc., 42:2621 [1983]; and A. Roberts et al., Proc. Natl. Acad. Sci. U.S.A., 83:4167 [1986]), as well as epithelia (T. Matsui et al., Proc. Natl. Acad. Sci. U.S.A., 83:2438 [1986]and G. Shipley et al. Cancer Res., 46:2068 [1986]). Moreover, TGF-β has been described as a suppressor of cytokine (e.g., TNF-α) production (Espevik et al., J. Exp. Med., 166: 571–576 [1987]) and as a promoter of cachexia (Beutler and Ceramic, New Eng. J. Med., 316: 379ff [1987]).

TGF-β is multifunctional, since it can either stimulate or inhibit cell proliferation, can either stimulate or inhibit differentiation, and can either stimulate or inhibit other critical processes in cell function (M. Sporn, Science 233:532 [1986]):

The multifunctional activity of TGF-β is modulated by the influence of other growth factors present together with the TGF-β. TGF-β can function as either an inhibitor or an enhancer of anchorage-independent growth, depending on the particular set of growth factors, e.g., EGF or TGF-α, operant in the cell together with TGF-β (Roberts et al., Proc. Natl. Acad. Sci. U.S.A., 82:119 [1985]). According to Brinkerhoff et al., Arthritis and Rheumatism, 26:1370 (1983), TGF-β can act in concert with EGF to cause proliferation and piling up of normal (but not rheumatoid) synovial cells. Furthermore, Chua et al., J. Biol. Chem., 260:5213–5216 [1983]reported that TGF-β induced collagenase secretion in human fibroblast cultures, and A. Tashjian et al., Proc. Natl. Acad. Sci. U.S.A., 82:4535 [1985] observed that TGF-β stimulated the release of prostaglandins and mobilization of calcium. TGF-β also has been reported to inhibit endothelial regeneration (R. Heimark et al., Science, 233:1078 [1986]).

U.S.S.N. 500,833, supra, relates to the use of TGF-β to repair tissue in animals, in particular for use in accelerating wound healing by stimulating cell proliferation. In addition, Sporn et al., Science, 219: 1329–1331 (1983) and U.S. Pat. Nos. 4,810,691 and 4,774,228 describe the use of TGF-β for promoting connective tissue deposition.

U.S. Ser. No. 07/116,101 filed Nov. 3, 1987, corresponding to EP Pub. 269,408, published June 1, 1988, and EP Pub. 213,776, corresponding to U.S. Pat. No. 4,806,523, disclose use of TGF-β as an immunosuppressant, to treat inflammatory diseases such as rheumatoid arthritis.

It has been found that septic shock and invasive infection are diseases caused by humoral mediators of both exogenous and endogenous origin. Thus, release of tumor necrosis factor (TNF), followed by interleukin-1 (IL-1) and interferon-gamma (IFN-γ), participates in the cascade of events noted in Gram-negative sepsis. Hesse et al., Surg. Gynecol. Obstet., 166: 147–153 (1988); Michie et al., N.Eng.J.Med., 318: 1481–1486 (1988); Espevik et al., J. Immunol., 140: 2312–2316 (1988).

Antibodies to TNF were found to protect mice from the lethal effect of endotoxin (Beutler et al., Science, 229: 869–871 (1985)). In addition, anti-cachectin/TNF monoclonal antibodies administered two hours before bacterial infusion conferred protection against septic shock and death in baboons. Tracey et al., Nature, 330:662–664 (1987). However, it has also been suggested that TNF and IL-1 participate in the mediation of endotoxin.induced enhancement of nonspecific resistance to intraabdominal infection and radiation sickness Urbaschek et al., Rev. Infect Dis., 9: S607–S615 (1987).

Monoclonal antibodies directed against endotoxin or its components have been evaluated for their utility in immunotherapy of Gram-negative sepsis. Thus, for example anti-core lipopolysaccharide (E. coli) has been reported to reduce mortality significantly in severely septic patients (E. Zeigler et al., N. Eng. J. Med., 307: 1225 (1982)). Also, murine and human monoclonal antibodies directed against the core lipopolysaccharide of the endotoxin were found to exert protection during Gram-negative bacterial sepsis in animals. Dunn, Transplantation, 45: 424–429 (1988); EP Publ. No. 183,876 published June 11, 1986; EP Publ. No. 174,204 published Mar. 12, 1986. Antibodies directed against lipid A also had a protective effect in humans. Jaspers et al., Infection 15 Suppl. 2: S89–95 (1987). Antibodies to the J5 mutant of E. coli are reported to be protective against septic shock in animals and humans. Cohen et al., Lancet, 1:8–11 (1987); Law and Marks, J. Infect. Dis., 151: 988–994 (1985). Antibodies to endotoxin core glycolipid were found to prevent the serious consequences of Gram-negative infections in surgical patients. Baumgartner et al., Lancet, 2: 59–63 (1985). In addition human monoclonal antibodies to P. aeruzinosa exotoxin A and exoenzyme S have been described as useful for this purpose. U.S. Pat. No. 4,677,070 issued June 30, 1987 and EP 243,174 published Oct. 28, 1987, respectively.

The clinical utility of these approaches using antibodies is being evaluated, but it is believed that they may suffer from some disadvantages such as unfavorable kinetics, biological half-life, and the potential for anti-idiotypic antibody generation that would neutralize the therapeutic antibody (in the case of human antibodies). In addition this immunotherapy only interdicts an early-stage effector.

It is an object of this invention to provide methods and compositions for the effective therapy and prevention of septic shock that do not rely on monoclonal antibody therapy.

This and other objects will become apparent to one of ordinary skill in the art.

SUMMARY OF THE INVENTION

These objects are achieved, in one aspect, by a method comprising administering to a patient suffering from or at risk of septic shock a pharmaceutically effective amount of transforming growth factor-beta (TGF-β).

In another aspect, this invention provides a composition for the treatment or prevention of septic shock comprising a pharmaceutically effective amount of transforming growth factor-beta (TGF-β) and a pharmaceutically effective amount of a substance selected from the group consisting of mafenide acetate, an antimicrobial agent, a sympathomimetic amine, a corticosteroid, an anti-coagulant, an anti-inflammatory agent, a diuretic, an antibody against tumor necrosis factor, an antibody against lipid A, an antibody against endotoxin core glycolipid, an antibody against J5 mutant of E. coli, an antagonist to tumor necrosis factor, an antagonist to interleukin-1, and a mixture of two or more of these substances.

BRIEF DESCRIPTION OF THE DRAWINGS

FIGS. 1a and 1b show the cDNA sequences and deduced amino acid sequences of porcine and human TGF-$\beta_3$, respectively. The 112 amino acid sequence of mature TGF-$\beta_3$ (overlined) constitutes the C-terminus of the precursor and is preceded by four basic residues (+). The precursor segment contains four overlined potential N-glycosylation sites. All cysteine residues are shaded. The AATAAA (FIG. 1a) and the related AG-TAAA (FIG. 1b) sequence close to the 3' end of the cDNA and preceding the polyadenylation site are underlined. FIG. 1c shows the homology between the imputed amino acid sequences of the human (h) and porcine (p) TGF-$\beta_3$ precursors. The asterisks mark identical residues, while a dot indicates a conservative amino acid replacement. The mature TGF-$\beta_3$ sequences are boxed. FIG. 2 shows the N-termini for selected forms of TGF-$\beta$. The letters h, p and b stand for human, porcine and bovine, respectively. Non-homologous residues are designated by a period over the residue in question.

DESCRIPTION OF THE PREFERRED EMBODIMENTS

Figure 3:
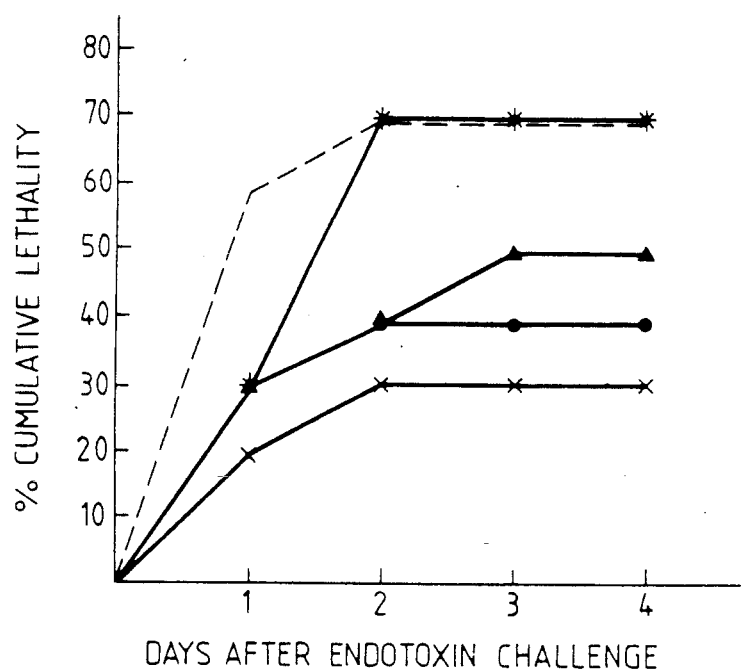
FIG. 3 shows the percent cumulative lethality of mice over time upon treatment with recombinant human TGF-$\beta$ or recombinant human IL-1$\alpha$ versus the PBS control at various doses and times relative to challenge with endotoxin.

As used herein, the expression "septic shock" refers to a condition primarily caused by bacteremic Gram-negative infection of a patient. This pathologic condition, of which endotoxin shock is a subset, is characterized by such symptoms as irreversible cardiovascular collapse and critical organ failure. In addition, the patient ordinarily experiences hyperventilation, skin lesions, and hypotension, and in certain instances, fever, chills, fall in urine output, and decrease in circulating platelet levels, jaundice, acidosis, bleeding, and hypoxia. Examples of Gram-negative bacteria responsible for septic shock include E. coli, including, e.g., the J5 mutant of E. coli (having only core determinants in its endotoxin, analogous to an Rc mutant), Pseudomonas aeruginosa, Aeromonas hydrophila, Yersinia pestis, and species from Klebsiella-Enterobacter, Salmonella, Hemoohilus, Proteus, and Serratia. Each species may produce different symptoms in the patient.

At the present time five highly homologous forms of TGF-$\beta$ have been identified, TGF-$\beta_1$, TGF-$\beta_2$, TGF-$\beta_3$, TGF-$\beta_4$, and TGF-$\beta_5$. 304 N-termini for the first three of these forms are set forth in FIG. 2. Reference to TGF-$\beta$ herein will be understood as reference to any one of these identified forms as well as others identified in the future, their alleles, and their predetermined amino acid sequence variants, so long as they are effective in the method described herein.

As can be seen from FIGS. 1a-1c, the mature TGF-$\beta_3$ amino acid sequence contains a large number of cysteine residues, at least some of which apparently are involved in interchain crosslinking in forming the homodimeric TGF-$\beta$ that is recovered from natural sources. The rest of the precursor contains only two cysteine residues. The complete TGF-$\beta_3$ precursor contains several pairs of basic residues that could also undergo post-translation cleavage and give rise to separate polypeptide entities.

Comparison of the porcine and human TGF-$\beta_3$ precursor sequences (see FIG. 1c) reveals a 90% amino acid identity. The amino acid sequences predicted from the human and porcine cDNA sequences are 410 and 409 amino acids long, respectively, and have a C-terminal sequence that resembles the previously established sequences for mature TGFs-$\beta$. The C-terminal 112 amino acid sequence has about 80% similarity to the porcine and human TGF-$\beta_1$ sequence and shares a similar degree of homology with the sequence of TGF-$\beta_2$.

In accordance with the method of this invention, the TGF-$\beta$. is administered prophylactically or therapeutically, i.e., before, simultaneous with, or after the infection has set in. The TGF-$\beta$ may be used passively to treat individuals who suffer from septicemia or are at risk with respect to bacteremic Gram-negative infection. Patients at risk include those receiving immunosuppressive therapy and those suffering from severe thermal burns or other serious injuries, cystic fibrosis, renal failure, or cancer, or are undergoing extensive surgical procedures or organ transplantation. One possible treatment is for chronic endobronchitic infection endemic in cystic fibrosis patients.

It is within the scope hereof to employ TGF-$\beta$ from animals other than humans, for example, porcine or bovine sources, to treat humans. Likewise, if it is desirable to treat other mammalian species such as domestic and farm animals and sports or pet animals, human TGF-$\beta$, as well as TGF-$\beta$ from other species, is suitably employed. In one instance of animal treatment, dairy cows are treated for acute coliform mastitis infections by using TGF-$\beta$ to remove and neutralize the effects of endotoxin. Thus, the term "patient" as used herein refers to all mammals, not just humans.

The TGF-$\beta$ is administered to the patient by any suitable technique, including parenteral and, if desired for localized bacteria, intralesional administration, preferably parenteral administration. The specific method of administration will depend, e.g., on whether the administration is therapeutic or prophylactic. Thus, in view of the therapeutic urgency attendant frank shock, the TGF-beta is preferably intravenously infused at the same time as solutions used for initial volume expansion. However, prophylaxis is generally accomplished, e.g., by intramuscular or subcutaneous administration or other parenteral administration, including intraarterial and intraperitoneal administration, preferably intravenous or intraperitoneal.

The TGF-$\beta$ compositions to be used in the therapy will be formulated and dosed in a fashion consistent with good medical practice taking into account the clinical condition of the individual patient, the cause of the septic shock, whether the TGF-$\beta$ is used for therapy of frank shock or prophylaxis of incipient septic shock, the site of delivery of the TGF-$\beta$, the method of administration, the scheduling of administration, and other factors known to practitioners. The "effective amount" for purposes herein is thus determined by such considerations.

As a general proposition. the total pharmaceutically effective amount of the TGF-β administered parenterally per dose will be in the range of approximately 1 μg/kg to 1 mg/kg of patient body weight once per day. although, as noted above, this will be subject to a great deal of therapeutic discretion. The key factor in selecting an appropriate dose and scheduling is the result obtained. Relatively higher doses may be needed initially for the treatment of profound shock, i.e., for patients in acute renal failure or respiratory distress, or having severely depressed blood pressure (mean arterial pressure below about 60 mm Hg).

The TGF-β is used in an activated form as well as in latent forms for slow-release formulations. Preferably, the TGF-β is activated, as by such methods as exposure to acidic or basic pH values, sodium dodecyl sulfate, or high concentrations of urea, as described, e.g., in Miyazono et al. *J. Biol. Chem.*, 263: 6407-6415 (1988), the disclosure of which is incorporated herein by reference. For example, the TGF-β may be treated with acid to give activity at pH below 6, preferably below 5.5, or incubated with 0.02% SDS or 8 M urea.

For parenteral administration, the TGF-β is formulated generally by mixing it at the desired degree of purity, in a unit dosage injectable form (solution, suspension, or emulsion), with a physiologically acceptable carrier, i.e., one that is non-toxic to recipients at the dosages and concentrations employed. Preferably the carrier is a parenteral carrier. Examples of such carrier vehicles include water, saline, Ringer's solution, dextrose solution, and 5% human serum albumin. Non-aqueous vehicles such as fixed oils and ethyl oleate are also useful herein, as well as liposomes. Generally, the carrier can contain minor amounts of additives such as substances that enhance isotonicity and chemical stability, e.g., buffers and preservatives, as well as low molecular weight (less than about 10 residues) polypeptides, proteins, amino acids, carbohydrates including glucose or dextrans, chelating agents such as EDTA, or other excipients. The TGF-β is typically formulated in such vehicles at a concentration of about 0.1 mg/ml to 100 mg/ml at pH range 4 to 6.

TGF-β for use in therapeutic administration must be sterile. This is readily accomplished by sterile filtration through (0.2 micron) membranes. TGF-β ordinarily will be stored as an aqueous solution since it is highly stable to thermal and oxidative denaturation although lyophilized formulations for reconstitution are acceptable.

TGF-β therapy or prophylaxis is suitably combined with other proposed or conventional therapies or prophylactic treatment for septic shock. For example, for treatment of burns, the TGF-β therapy may be delivered by separate means, simultaneously with and by the same administration route as other substances such as mafenide acetate, antibiotics, or anti-microbial agents that inhibit bacterial colonization of the burn wound surface. Other therapies that can be combined with TGFβ therapy include primary therapeutic agents, for example potent anti-microbial agents such as aminoglycosides (such as amikacin, tobramycin netilmicin, and gentamicin), cephalosporin, related beta.lactam agents such as moxalactam, carbopenems such as imipenem, monobactam agents such as aztreonam, ampicillin and broad-spectrum penicillins (e.g., penicillinase-resistant penicillins, ureidopenicillins, or antipseudomonal penicillins) that are active against *P. aeruginosa*, *Enterobacter* species, indole-positive *Proteus* species, and *Serratia*.

Various adjunctive agents in the treatment of septic shock also are useful in combination with TGF-β. These include sympathomimetic amines (vasopressors) such as norepinephrine, epinephrine, isoproterenol, dopamine, and dobutamine; antiinflammatory agents such as methylprednisolone, and corticosteroids such as betamethasone, hydrocortisone, methylprednisolone, or dexamethasone; anti-coagulants such as heparin or coumadine-type drugs for certain conditions and schedules; diuretics such as furosemide or ehacrynic acid; an antagonist of opiates and betaendorphins such as naloxone; an antagonist of tumor necrosis factor or of interleukin-1; phenothiazines; anti-histamines; antiinflammatory agents such as indomethacin and phenylbultazone; glucagon; α-adrenergic blocking agents, vasodilators; plasma expanders, packed red blood cells; platelets; cryoprecipitates; fresh frozen plasma; clindamycin; and antibodies to the J5 mutant of *E. coli*, to lipid A, or to endotoxin core glycolipids. Methods for preparing the antibodies are described in the articles provided *supra*, and TNF-α antagonists are described in U.S.S.N. 898,272 filed Aug. 20, 1986, now abandoned, the disclosures of all of which are incorporated herein by reference.

Therapeutic measures that can be used in conjunction with administering the TGF-β include granulocyte transfusion and percutaneous drainage of abdominal abscesses. In addition, prophylactic measures that are useful in conjunction with the TGF-β involve, e.g., barrier isolation to minimize contact of the patient with infectious agents, use of prophylactic anti-microbial agents of a systemic form, active or passive immunoprophylaxis with typespecific or cross-reactive antibodies, and augmentation of the host granulocyte pool with prophylactic granulocyte transfusions.

It is not necessary that such cotreatment drugs be included in the TGF-β compositions per se although this will be convenient where such drugs are delivered by the same administration route, e.g., antagonists to the activity of TNF-α or IL-1, or the abovedescribed neutralizing antibodies.

When employed together with the TGF-beta, such agents (other than antibiotics) preferably are employed in lesser dosages than when used alone. A typical combined composition will contain greater than about 0.5 nmole, generally about 0.05 μmole, of TGF-beta, about from 0.0003 to 0.05 μmole of anti-lipopolysaccharide IgG, and about from 5 to 60 μg of dopamine in about from 10 to 1000 ml of a suitable intravenous or intraperitoneal fluid such as lactated Ringer's solution. This composition then is piggybacked onto an infusion serving primarily for plasma expansion and administered to control shock.

The invention will be more fully understood by reference to the following examples. They should not, however, be construed as limiting the scope of the invention. All literature citations are incorporated by reference.

EXAMPLE 1

The experiments described below were designed to determine the effects of TGF-β on LPS-induced TNF-α production in vivo.

Five groups of female BALB/c mice, 6-8 weeks old, with six mice per group, were treated as follows:

Group A: LPS (E. coli LPS 026:B6. Sigma Chemical Co., St. Louis, MO) at 5 μg/mouse was administered iv at 5 μ/mouse.

Group B: Phosphate buffered saline was administered at four hours before time 0 (when LPS was administered) and at time 0.

Group C: TGF-β at 1 μg/mouse was administered iv at 100 μl/mouse at four hours prior to administration of LPS (at time 0) at 5 μg/mouse iv at 100 μl/mouse. The TGF-β employed in this experiment was human TGF-β1 obtained recombinantly as described in EP Publ. No. 200,341 published Dec. 10, 1986, the disclosure of which is incorporated herein by reference. The diluent employed for the TGF-β was 20 mM sodium acetate buffer, pH 4.

Three mice per group were sacrificed and bled 60 minutes after LPS treatment and the other three mice per group were sacrificed and bled 90 minutes after LPS treatment. The sera from the mice were harvested and stored at −70° C. Then the amount of TNF-α in the sera was measured by subjecting the sera to the MTT tetrazolium cytotoxicity assay using WEHI 164 clone 13 mouse fibrosarcoma cells described by Espevik et al., J.Immunol.Meth., 95: 99–105 (1986). The results are shown in the table below:

| Test No. | Agent | TNF-α (pg/ml) | Average TNF-α (pg/ml) per every three experiments |
|---|---|---|---|
| 1 | LPS | 117 +/− 21 | |
| 2 60' | LPS | 410 +/− 33 | 273 +/− 85 |
| 3 | LPS | 293 +/− 40 | |
| 4 | LPS | 525 +/− 4 | |
| 5 90' | LPS | 312 +/− 0 | 369 +/− 78 |
| 6 | LPS | 270 +/− 10 | |
| 7 | PBS | <0.2 | |
| 8 60' | PBS | <0.2 | |
| 9 | PBS | <0.2 | |
| 10 | PBS | <0.2 | |
| 11 90' | PBS | <0.2 | |
| 12 | PBS | <0.2 | |
| 13 | 1 μg TGF-β | 72 +/− 6 | |
| 14 60' | 1 μg TGF-β | 409 +/− 19 | 236 +/− 97 |
| 15 | 1 μg TGF-β | 227 +/− 14 | |
| 16 | 1 μg TGF-β | 97 +/− 8 | |
| 17 90' | 1 μg TGF-β | 203 +/− 17 | 241 +/− 97 |
| 18 | 1 μg TGF-β | 423 +/− 47 | |
| 19 | 5 μg TGF-β | 443 +/− 30 | |
| 20 60' | 5 μg TGF-β | 389 +/− 20 | 649 +/− 233 |
| 21 | 5 μg TGF-β | 1114 +/− 72 | |
| 22 | 5 μg TGF-β | 601 +/− 2 | |
| 23 90' | 5 μg TGF-β | 379 +/− 40 | 561 +/− 324 |
| 24 | 5 μg TGF-β | 705 +/− 68 | |
| 25 | 10 μg TGF-β | 1039 +/− 64 | |
| 26 60' | 10 μg TGF-β | 401 +/− 76 | 791 +/− 197 |
| 27 | 10 μg TGF-β | 935 +/− 67 | |
| 28 | 10 μg TGF-β | 2292 +/− 24 | |
| 29 90' | 10 μg TGF-β | 2118 +/− 83 | 1842 +/− 365 |
| 30 | 10 μg TGF-β | 1118 +/− 13 | |

The results indicate that TGF-β inhibits endotoxin-induced TNF-α production at lower doses; at higher doses it significantly enhances TNF-α production.

A similar experiment using female NMRI mice revealed the following: Whereas no TNF-α was detectable in controls and in mice two hours after 5 μg of TGF-β was administered ip, 770 U/ml of TNF-α were detected two hours after 10 μg of endotoxin was administered and 240 U/ml of TNF-α were detected when TGF-β (5 μg) was injected simultaneously with 10 μg of endotoxin.

EXAMPLE 2

First Endotoxin Tolerance Model

Five groups of NMRI female mice (weighing 28.2 +/−3.4 g and 9–10 weeks old) were used, each group consisting of ten animals. The mice were permitted food ad libitum. One group received 5 μg of TGF-β at −24 hours, the second at the time of endotoxin administration, the third at −24 hours and again at the time of endotoxin administration, and the fourth received 2000 units of recombinant human IL-1α at −24 hours. The fifth group was the control which consisted of mice treated with phosphate buffered saline at 0.5 ml at −24 hours. The administration of TGF-β and IL-1 was intraperitoneal and the administration of the endotoxin was intravenous at 200 μg or 0.2 ml per injection.

The TGF-β employed in this experiment was the same as that used in Example 1. After purification, the TGF-β was formulated in acetic acid buffer at pH 5 to 5.4. The IL-1 was recombinant human IL-1α obtained from Dr. Lomedico at Roche Pharmaceuticals, Nutley, N.J (As IL-1α and IL-1β bind to the same receptor, similar results are expected using IL-1β.) The endotoxin was extracted from E. coli 0111:B4 (publicly available) by the method described by Boivin et al., C.R. Soc. Biol., 114: 307–310 (1933), Boivin et al., C.R. Soc. Biol., 115: 304 (1934), and Boivin et al., Rev.d'Immunolozie, 1: 553 (1935), the disclosures of all of which are incorporated herein by reference.

The percent mortality of the mice was determined after one, two, three, and four days. The results of this study are shown in Table I, and the plots of the percent cumulative lethality of each group of mice versus days is shown in FIG. 3, where the crosses are the TGF-β pretreatment, the closed circles are the TGF-β pretreatment/simultaneous treatment, the closed triangles are the TGF-β simultaneous treatment, the dashed line is the IL-1 treatment, and the asterisks are the PBS control.

TABLE I

| Agent | Dose | Time | Percent Cumulative Lethality at Day 4 After Challenge |
|---|---|---|---|
| TGF-β | 5 μg | −24 hr. | 30 |
| TGF-β | 5 μg/5 μg | −24/0 hr. | 40 |
| TGF-β | 5 μg | 0 hr. | 50 |
| IL-1 | 2000 units | −24 hr. | 70 |
| PBS (control) | 0.5 ml | −24 hr. | 70 |

Percent mortality was reduced in all cases over the control when TGF-β was employed. The percent mortality was the lowest when the TGF-β was administered once at −24 hours.

Second Endotoxin Tolerance Model

Figure 4:
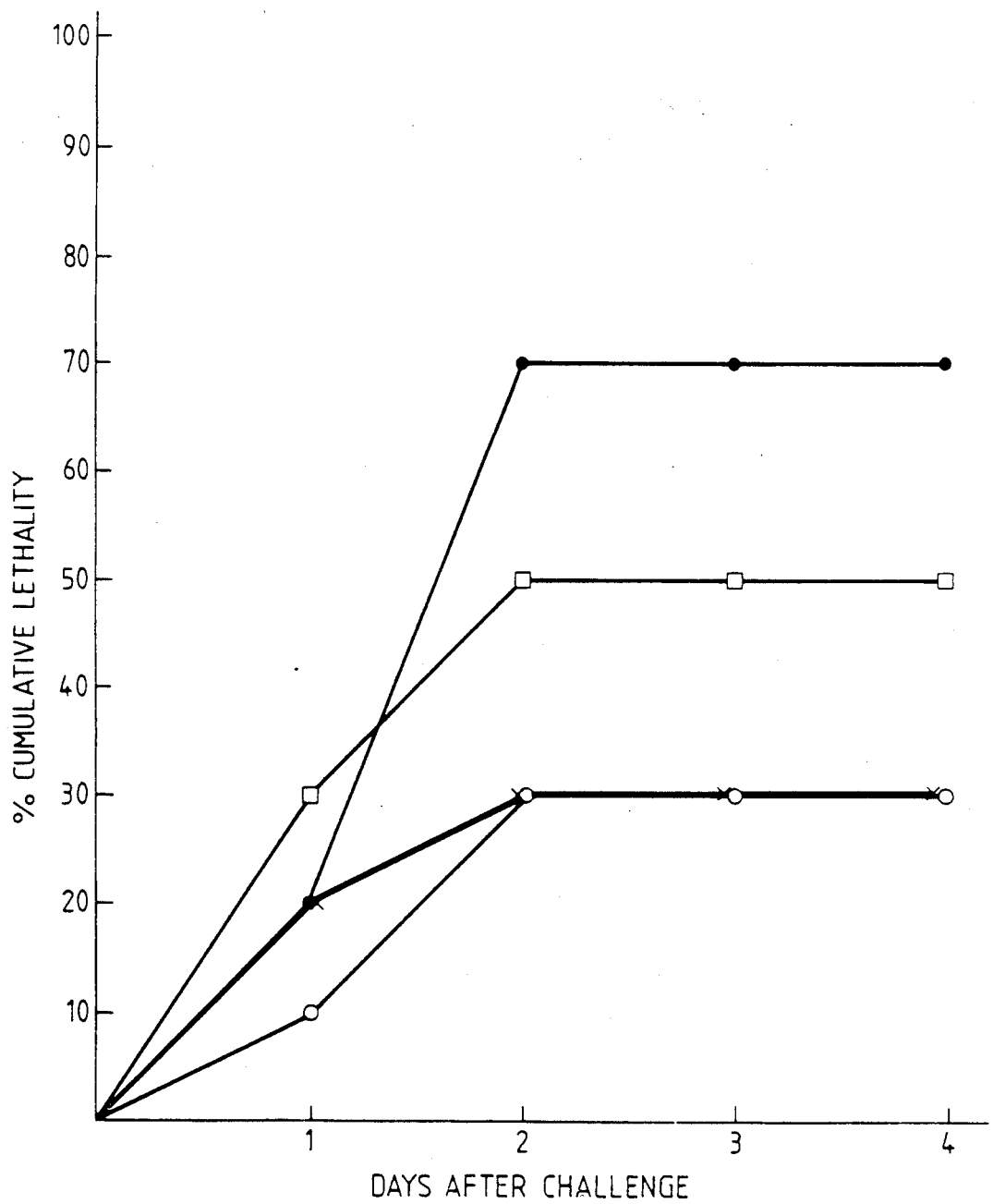
FIG. 4 shows a separate study from FIG. 3 on the percent cumulative lethality of mice over time upon treatment with recombinant human TGF-$\beta$ versus the PBS control at various doses and times relative to challenge with endotoxin.

The above experiment was repeated using a 190 μg/0.2 ml iv dose of the endotoxin, groups of ten mice, and varying ip doses of the TGF-β used above (i.e., 5 μg/0.25 ml at 24 hours before endotoxin administration, 5 μg/0.25 ml simultaneously with endotoxin administration and 10 μg/0.25 ml simultaneously with endotoxin administration). The percent cumulative lethality profiles from 1 to 4 days after endotoxin challenge are shown in FIG. 4, where the open squares are the control, the crosses are the TGF-β 24 hours before endotoxin administration, the open circles are 5 μg TGF-β simultaneously with endotoxin administration, and the closed circles are 10 μg TGF-β simultaneously with endotoxin administration. The 10 μg/mouse dose of TGF-β was found to enhance mortality after endotoxin administration.

Septicemia/Cecal Ligation Model

Because of the potential immunosuppressive effects of TGF-β a study was performed to see if TGF-β would increase the susceptibility of mice to bacterial infection due to a puncture wound.

TGF-β and IL-1 were administered separately, intraperitoneally, at 5 μg dose of TGF-β and at 2000 units dose of IL-1 once at 24 hours prior to surgery on the mice, performed as described below. A control was employed consisting of PBS administered intraperitoneally at 0.5 ml.

Experiments were performed in groups of seven female NMRI mice (weighing 28.2 +/−3.4 g), which were permitted food ad libitum. A 0.5.-cm midline incision was made in etherized animals, and the cecums were carefully exteriorized. Each cecum was filled with feces by milking stool into it from the ascending colon and then ligated just below the ileocecal valve to retain bowel continuity. After two punctures of the cecum with a 20-gauge needle followed by slight pressure to force the appearance of feces, the cecum was returned to the peritoneal cavity and the incision closed with a clamp. Finally, the operated mice received 1 ml of saline subcutaneously.

Figure 5:
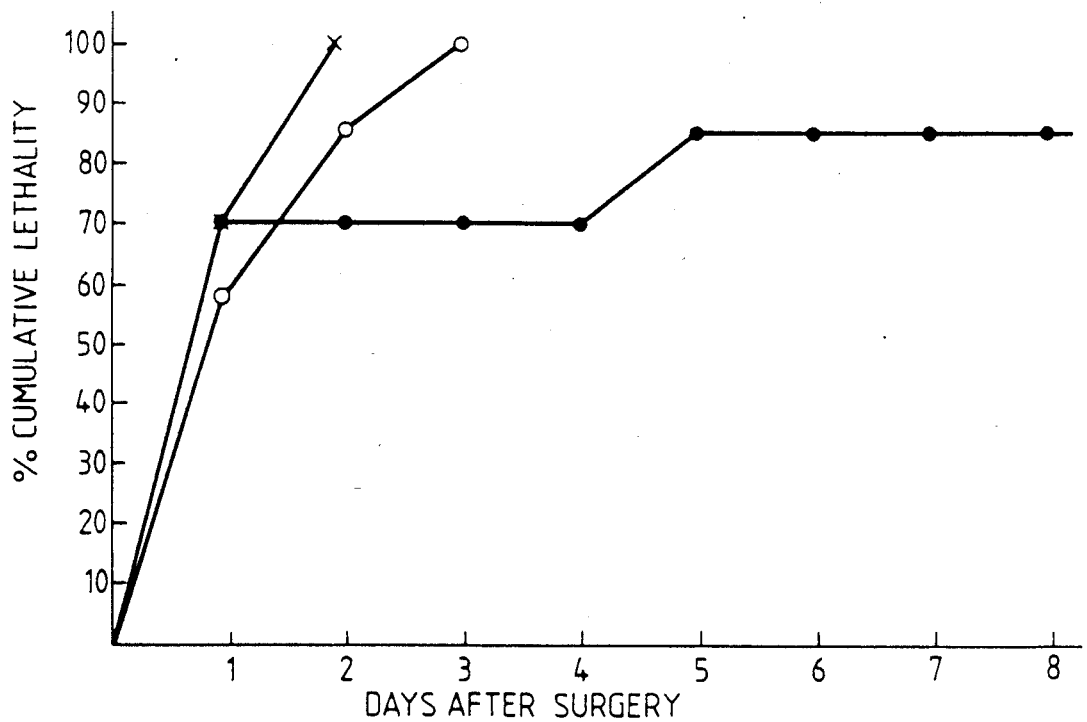
FIG. 5 shows the percent cumulative lethality upon treatment of mice with recombinant human TGF-$\beta$ or recombinant human IL-1$\alpha$ versus the PBS control after cecal ligation and puncture surgery.

The mice were then evaluated for percent lethality every day for eight days following the surgery. The results are shown in FIG. 5. The open circles represent the control, the closed circles represent the IL-1, and the crosses represent TGF-β. IL-1 was found to reduce mortality relative to the control, whereas TGF-β did not decrease or substantially increase mortality relative to the control. Thus, TGF-β, which is a known immunosuppressive agent, did not increase the mortality of the mice.

EXAMPLE 3

Effects on E. coli Septic Shock

Recent evidence suggests that tumor necrosis factor-alpha is a key mediator of the lethal effects of overwhelming bacterial infection. The administration of antibodies to TNF-α, in contrast, protects animals from the lethal effects of septic shock. As TGF-β can decrease endotoxin-stimulated release of TNF-α in vitro and in vivo (*J. Exo. Med.*, 166: 571 (1987)), the ability of TGF-β to inhibit E. coli-induced septic shock was investigated, as described below:

Fischer 344 male rats of 180–200 g were administered intraperitoneally 10 μg of either recombinant TGF-β1 (prepared as described in Example 1 in a buffer comprising 20 mM sodium acetate pH 5 with 0.1% weight:volume human serum albumin), recombinant TGF-β2 (obtained from Dr. Adriano Fontana, Zurich, Switzerland, as a lyophilized pellet - - - see WO 88/03807 published June 2, 1988 - - - and resuspended in 1% acetic acid), or diluent control (consisting of a buffer of 20 mM sodium acetate with 0.1% human serum albumin). 72 hours later, pathogenic E. coli ($1-3 \times 10^9$) was given. The results are indicated below:

| Substance | Mortality (dead/total) hours after *E. coli* Challenge | | | |
|---|---|---|---|---|
| | 12 | 24 | 48 | 72 |
| Control | 5/30 | 8/30 | 17/30 | 18/30 |
| rTGF-β1 | 0/30 | 7/30 | 12/30 | 13/30 |
| Control | 2/12 | 6/12 | 11/12 | 11/12 |
| rTGF-β2 | 0/12 | 4/12 | 5/12 | 5/12 |

It was found that 1–25 μg of TGF-β1 in this rat model was effective in reducing mortality versus the diluent control, however, a dose of 50 μg of TGF-β1 increased mortality versus the control. This is consistent with the dose-dependent results from the experiments reported in Example 1.

Serum TNF-α Levels

In parallel experiments reduced serum TNF-α (and IL-6) levels were determined two hours after E. coli injection by the L-M in vitro bioassay described by Kramer et al., *J. Immunol. Meth.*, 93: 201–206 (1986). The serum TNF-α levels were found to be 22 +/− 4.9 units/ml (5 rats) versus 87.5 +/−18.6 units/ml (5 rats) for controls, $p < 0.01$.

These data suggest that in vivo rTGF-β pretreatment can reduce the peak TNF-α response to E. coli challenge as well as delay and reduce the mortality observed with septic shock.

What is claimed is:

1. A method comprising administering to a patient suffering from or at risk of septic shock a pharmaceutically effective amount of transforming growth factor-beta.

2. The method of claim 1 wherein the pharmaceutically effective amount is about 5 μg/kg to 1 mg/kg of patient body weight and the TGF-β is administered parenterally on a daily basis.

3. The method of claim 1 wherein the TGF-β is administered to a patient having a microbial infection but not yet showing symptoms of septic shock.

4. The method of claim 3 wherein the TGF-β is administered by intravenous infusion or intraperitoneally.

5. The method of claim 2 wherein the TGF-β is administered intraperitoneally to a patient having a microbial infection but not yet showing symptoms of septic shock.

6. The method of claim 1 wherein the TGF-β is administered with a pharmaceutically effective amount of mafenide acetate, an anti-microbial agent, a sympathomimetic amine, an anti-inflammatory agent, a corticosteroid, an anti-coagulant, a diuretic, an antibody against tumor necrosis factor, an antibody against lipid A, an antibody against endotoxin core glycolipid, an antibody against J5 mutant of *E. coli*, an antagonist to tumor necrosis factor, an antagonist to interleukin-1, or a mixture of two or more of these substances.

7. The method of claim 1 wherein the TGF-β is human TGF-β.

8. The method of claim 1 wherein the TGF-β is TGF-β1, TGF-β2, or TGF-β3.

9. The method of claim 7 wherein the TGF-β is TGF-β1, TGF-β2, or TGF-β3.

* * * * *